(12) United States Patent
Warlick et al.

(10) Patent No.: US 7,988,648 B2
(45) Date of Patent: *Aug. 2, 2011

(54) PANCREAS REGENERATION TREATMENT FOR DIABETICS USING EXTRACORPOREAL ACOUSTIC SHOCK WAVES

(75) Inventors: John Warlick, Woodstock, GA (US); Wolfgang Schaden, Vienna (AT); Reiner Schultheiss, Illighausen (CH)

(73) Assignee: General Patent, LLC, Marietta, GA (US)

( * ) Notice: Subject to any disclaimer, the term of this patent is extended or adjusted under 35 U.S.C. 154(b) by 1199 days.

This patent is subject to a terminal disclaimer.

(21) Appl. No.: 11/676,761

(22) Filed: Feb. 20, 2007

(65) Prior Publication Data

US 2007/0142753 A1    Jun. 21, 2007

Related U.S. Application Data

(63) Continuation-in-part of application No. 11/122,154, filed on May 4, 2005, now Pat. No. 7,470,240, and a continuation-in-part of application No. 11/071,156, filed on Mar. 4, 2005, now abandoned.

(51) Int. Cl.
*A61H 1/02* (2006.01)
(52) U.S. Cl. .................................. 601/2; 601/4; 600/437
(58) Field of Classification Search ................... 601/2, 4; 600/437, 427
See application file for complete search history.

(56) References Cited

U.S. PATENT DOCUMENTS

| | | |
|---|---|---|
| 3,951,140 A | 4/1976 | Eggleton et al. |
| 4,539,989 A | 9/1985 | Forssmann et al. |
| 4,807,627 A | 2/1989 | Eisenmenger |
| 4,868,161 A | 9/1989 | Roberts |
| 4,905,671 A | 3/1990 | Senge et al. |

(Continued)

FOREIGN PATENT DOCUMENTS

DE    19721218    11/1998

(Continued)

OTHER PUBLICATIONS

Press Release: FDA approves once-daily Januvia the first and only DPP-4 inhibitor available int eh united states for type 2 diabetes: http://www.januvia.com/sitagliptin_phosphate/januvia/hcp/press/index.jsp, Oct. 17, 2006.

(Continued)

*Primary Examiner* — Tse Chen
*Assistant Examiner* — John F Ramirez
(74) *Attorney, Agent, or Firm* — David L King

(57) ABSTRACT

The method of stimulating a tissue of a subsurface organ is disclosed. The method has the steps of activating an acoustic shock wave generator or source to emit acoustic shock waves; and subjecting the tissue to the acoustic shock waves stimulating said tissue wherein the tissue is positioned within a path of the emitted shock waves and away from a geometric focal volume or point of the emitted shock waves. In one embodiment the emitted shock waves are divergent or near planar. In another embodiment the emitted shock waves are convergent having a geometric focal volume of point at a distance of at least X from the source, the method further comprising positioning the tissue at a distance less than the distance X from the source. The subsurface organ is a tissue having cells. The tissue is a part of the incretin system. The subsurface organ is preferably the pancreas of a diabetic or at risk diabetic patient. The treatment stimulates the pancreatic tissue by an analgesic effect on the nerves and a stimulation of the insulin producing islets.

23 Claims, 11 Drawing Sheets

U.S. PATENT DOCUMENTS

| | | | |
|---|---|---|---|
| 5,119,801 | A | 6/1992 | Eizenhoefer et al. |
| 5,173,295 | A | 12/1992 | Wehling |
| 5,174,280 | A | 12/1992 | Gruenwald et al. |
| 5,222,484 | A | 6/1993 | Krauss et al. |
| 5,314,457 | A | 5/1994 | Jeutter et al. |
| 5,419,335 | A | 5/1995 | Hartmann |
| 5,545,124 | A | 8/1996 | Krause et al. |
| 5,595,178 | A | 1/1997 | Voss et al. |
| 6,036,661 | A | 3/2000 | Schwarze et al. |
| 6,068,596 | A | 5/2000 | Weth et al. |
| 6,113,560 | A | 9/2000 | Simnacher |
| 6,186,963 | B1 | 2/2001 | Schwarze et al. |
| 6,368,292 | B1 | 4/2002 | Ogden et al. |
| 6,390,995 | B1 | 5/2002 | Ogden et al. |
| 6,544,987 | B2 | 4/2003 | Guo et al. |
| 6,881,409 | B2 | 4/2005 | Gold |
| 2002/0002345 | A1 | 1/2002 | Marlinghaus |
| 2003/0129154 | A1 | 7/2003 | McDaniel |
| 2004/0059265 | A1 | 3/2004 | Candy et al. |
| 2004/0162508 | A1 | 8/2004 | Uebelacker |
| 2005/0075587 | A1 | 4/2005 | Vago et al. |
| 2006/0051328 | A1 | 3/2006 | Johnson |
| 2006/0246044 | A1 | 11/2006 | Lutz et al. |

FOREIGN PATENT DOCUMENTS

| | | |
|---|---|---|
| DE | 10311659 | 9/2004 |
| EP | 0243947 | 4/1987 |
| EP | 1445758 | 8/2004 |
| WO | 2005075020 | 8/2005 |
| WO | 2006023498 | 2/2006 |

OTHER PUBLICATIONS

R.Meirer, et al; Extracorporal shock wave may enhance skin flap survival in an animal model; British Journal of Plastic Surgery; vol. 58, issue 1, Jan. 2005, pp. 53-57; copyright 2004; The British Association of Plastic Surgeons, published by Elsevier Ltd.

T.Nishida,et al; Extraporeal Cardiac Shock Wave Therapy Markedly Ameliorates Ischemia-Induced Myocardial Dysfunction in Pigs in Vivo; Circulation; Nov. 9, 2004; Circulation 2004; 110; pp. 3055-3061.

L.Gerdesmeyer, et al; Antibacterial Effects of Extracorporeal Shock WAves; World Fed for Ultrasound in Medicine & Biology; printed USA, Elsevier, vol. 31 No. 1, pp. 115-119, 2005.

G.Haupt, et al; Effect of Shock Waves on the Healing of Partial-Thickness Wounds in Piglets; Journal of Surgical Research, vol. 49, No. 1, pp. 45-48, Jul. 1990; Copyright 1990 by Academic Press Inc.

Jagadeesh, G., et al; "Novel applications of micro-shock waves in biological sciences"; J.Indian Inst. Sci. 2002, 82, pp. 1-10.

Theil, M, et al; "The use of shock waves in medicine-a tool of the modern OR; an overview of basic phyusical principles, history and research", Min Invas Ther & Allied Technol; 2000; 9(3/4) 247-253.

Huemer, Georg M., et al; "Comparison of the effectiveness of gene therapy with transforming growth factor-B or extracorporeal shock wave therapy to reduce ischemic necrosis in an epigastric skin flap model in rats"; Clinical Dept of Plastic and Reconstructive Surgery; Medical University Innsbruck Austria; Feb. 13, 2004; copyrt 2005 by the Wound Healing Society. ISSN: 1067-1927; wound rep reg 2005; 13:262-268.

PANCREAS REGENERATION TREATMENT FOR DIABETICS USING EXTRACORPOREAL ACOUSTIC SHOCK WAVES

RELATED APPLICATIONS

This application is a continuation in part of U.S. patent application Ser. No. 11/071,156 filed on Mar. 4, 2005 entitled "Pressure Pulse/Shock Wave Apparatus for Generating Waves Having Nearly Plane or Divergent Characteristics" and U.S. patent application Ser. No. 11/122,154 entitled "Pressure Pulse/Shock Wave Therapy Methods and an Apparatus for Conducting the Therapeutic Methods", the disclosures of which are incorporated herein by reference in their entirety.

TECHNICAL FIELD

This invention relates to the field of treating the pancreas of diabetic patients with acoustic pressure pulse shock waves generally. More specifically to treating the various abnormal conditions found in the pancreas of a diabetic using shock waves that are generated as either focused waves at high or low energy levels or non-focused waves at preferably low energy levels or a combination of such waves.

BACKGROUND OF THE INVENTION

On Dec. 20, 2006 the United Nations General Assembly passed a landmark resolution recognizing diabetes as a global pandemic. This is a first for a non-infectious disease. This resolution led by the International Diabetes Federation has brought global attention to a disease that affects 246 million people living with diabetes. On Nov. 14, 2007 the UN will observe the First World Diabetes Day.

The financial burden of diabetes is tremendous. The direct and indirect costs associated with both forms of diabetes, type 1 and type 2, in the United States during 2002 were estimated to be $132 billion. The average annual health care costs for a person with diabetes are $13,243, which is 2.4 times greater than those for an individual without diabetes. In 2002, 11 percent of national health care expenditures were directed to diabetes care. The costs of treating the complications of diabetes, which both forms of the disease share in common, account for much of the health care costs associated with the disease. Although estimates of the rates of diabetes have increased since 2002, the associated cost estimates have not yet been revised; hence, the economic data given here are conservative. Clearly, the economic and societal burden of diabetes has a profound impact on the Nation.

Type 1 diabetes is an autoimmune disease in which the body's own immune system attacks and destroys specialized cells of the pancreas called beta cells. Beta cells are found within tiny clusters called islets and produce the hormone insulin. Insulin is required for survival; it sends signals to the body's cells and tissues, telling them to absorb glucose to use as a fuel. Without this vital hormone, the cells and tissues do not absorb glucose and patients can starve to death, despite having high levels of glucose in their bloodstream. An interplay of genetic and environmental factors is responsible for the onset of type 1 diabetes (as well as type 2 diabetes). Having a family member with the disease puts one at higher risk for developing type 1 diabetes.

Type 1 diabetes differs from type 2 diabetes—type 2 is more commonly diagnosed in adulthood, is strongly associated with overweight and obesity and disproportionately affects minority populations. Although patients with type 1 diabetes require externally administered insulin to survive, type 2 diabetes patients may be treated with medications that make their tissues more sensitive to insulin or enhance insulin production or, in some cases, may be treated with insulin itself.

The treatment of patients with type 1 diabetes was revolutionized in 1921 with the discovery of insulin by a group of researchers at the University of Toronto. To this day, insulin therapy continues to save the lives of patients with type 1 diabetes by replacing the essential hormone what their bodies no longer adequately produce. However, insulin therapy, whether through injections or via a pump, is not a cure and it cannot prevent complications. To manage the disease, patients must carefully monitor their food intake and physical activity. They must perform painful finger sticks multiple times a day to draw blood and test their glucose levels. Based on this monitoring, patients often give themselves several shots of insulin a day, or calculate the correct amount of insulin to administer through their insulin pumps. This regimen is not just "once in a while;" it is every day of their lives. As many patients and their parents say; "There is never a day off from diabetes". Moreover, no matter how vigilant patients are at regulating their blood glucose levels, they can never achieve the fine tuned regulation provided by a healthy pancreas, which exquisitely senses and responds to insulin needs with precise timing.

In 1980 the development of the first animal model of type 1 diabetes that could be used to test drugs for type 1 diabetes; non-obese diabetic (NOD) mouse. Using these NOD mice, doctors from Toronto, the birthplace of insulin discovery, made a revolutionary discovery.

On Dec. 15, 2006, in Canada, a publication in Canada.com reported a Toronto scientist actually appeared to have cured diabetic mice by manipulating the nerves surrounding the insulin-producing islets. Dr. Dosch as early as 1999 concluded that there were surprising similarities between diabetes and multiple sclerosis a central nervous system disease. He suspected a link between the nerves and diabetes. In the article, Dr. Dosch and Dr. Salter used capsaicin, the active ingredient in hot peppers, to kill the pancreatic sensory nerves in mice that had the equivalent of Type 1 diabetes. Once the nerves were deactivated, the islets began producing insulin normally. They had discovered the nerves secrete neuropeptides that are instrumental in the proper functioning of the islets. The University of Calgary and the Jackson Laboratory in Maine found the nerves in diabetic mice were releasing too little of the neuropeptides, resulting in a "vicious cycle" of stress on the islets. In a trial they injected neuropeptide "substance P" in the pancreas of diabetic mice. The islet inflammation cleared up and the diabetes was gone with just one injection. In this study they also discovered that their treatments curbed the insulin resistance that is the hallmark of Type 2 diabetes, and that the insulin resistance is a major factor in Type 1 diabetes, suggesting the two illnesses are quite similar. This research has yet to be tested in clinical trials on humans, but if confirmed it may lead to an irradication of both Type 1 and 2 diabetes.

Solutions to the problem of diabetic disease often involve the use of medications. the most promising appear to be those that can enhance the natural body system called the incretin system, which helps regulate glucose by affecting the beta cells and alpha cells in the pancreas. These prescription medications called dipeptidyl peptidase-4 (DPP-4) inhibitors improve blood sugar control in patients with type 2 diabetes. Through DPP-4 inhibition this new class of drug works when the blood sugar is elevated due to beta-cell dysfunction and uncontrolled production of glucose by the liver due to alpha cell and beta cell dysfunction.

Preferably, these new classes of medications and treatments for diabetes can be more effective when initiated or alternatively combined with the novel use of acoustic shock wave treatments. It is therefore an object of the present invention to treat the pancreas or liver of diabetic diagnosed patients or at risk patients with a tissue regenerating shock wave treatment.

It is also an object of the present invention to provide a shock wave therapy that employs a more effective wave energy transmission, that is both simple to deploy and less target sensitive when compared to reflected focused waves.

It is a further object of the invention to provide a therapeutic treatment of a large target area for subsurface soft tissues of organs such as the pancreas or liver to treat diseases including, but not limited to diabetes.

C. J. Wang discovered that a variety of substances displaying high biological activity are released during and after the application of shock waves to tissue. The production of nitric oxygen (NO), vessel endothelial growth factor (VEGF), bone morphogenetic protein (BMP), and other growth factors have been demonstrated. Furthermore, Maier discovered a decline in the number of small-myelinized neurons after shock wave therapy, an observation that could explain the analgesic effect of shock wave therapy. As a consequence of these findings, the mechanistic model was increasingly relegated to a secondary role and supplanted by a microbiological model explaining the action of shock waves.

In practice the use of ESWT has been a results oriented science wherein a clear and accurate understanding of the actual healing process was neither understood nor fully appreciated. As a result a variety of treatments and uses of ESWT in mammals had heretofore never been tried or attempted or if tried, the outcomes were at best mixed.

A primary factor in the reluctance to use ESWT was that the believed threshold energy requirements were so high that the surrounding tissue would hemorrhage, exhibited by hematomas and bleeding around the treated site. This phenomenon is particularly known in the area of focused emitted waves designed for deep penetration into the patient. US patent publication 2005/0010140 recites the disadvantageous effects of cavitation phenomena can be controlled wherein the shock wave source is connected to a control means which controls the release frequency of shock waves as a function of pulse energy in such a manner that higher pulse energy correlates with lower release frequencies of the shock waves and vice versa. The avoidance of cavitation occurrences would it is postulated result in far less pain for the patient.

In US 2006/0246044 published on Nov. 2, 2006, Andreas Lutz of Dornier Med Tech Systems in Germany disclosed "Methods for Improving Cell Therapy and Tissue Regeneration in Patients With Cardiovascular Disease by Means of Shockwaves". In this application the use of shock waves is used in combination with cell therapy to assist in heart or neurological tissue regeneration.

The present invention recognizes the underlying beneficial attributes of ESWT are not now and may never be fully comprehended, however, under a more advanced molecular theory the authors of the present invention postulated a microbiological model suggesting the response mechanism to such treatment.

This model attempts to explain the effect of ESWT by postulating neovascularization of the treated tissue with simultaneous release of diverse growth factors. The enhanced metabolic activity taking place in the presence of these growth factors could be responsible for the healing of the chronically inflamed tissue while the decrease in afferent nerve fibers causes the analgesic effect.

The present inventors see that ESWT is a highly versatile therapeutic instrument. It can be used as a bioengineering tool to achieve effects such as the production of growth factors or as a surgical instrument to effect an extremely subtle type of denervation. In the field of traumatology, these properties are used primarily to treat fractures with non-union or delayed osseous union. ESWT is also becoming increasingly important for treating the early stages of osteochondritis dissecans. Heretofore the use of ESWT has never been used as a therapeutic instrument in the treatment of diabetes.

These and other applications of the present invention are described more fully as follows with first detailed description of shock wave therapeutic methods and then a detailed description of several shock wave devices and apparati for carrying out the methods.

SUMMARY OF THE INVENTION

The method of stimulating a tissue of a subsurface organ comprises the steps of activating an acoustic shock wave generator or source to emit acoustic shock waves; and subjecting the tissue to the acoustic shock waves stimulating said tissue when positioned within a path of the emitted shock waves and preferably away from a geometric focal volume or point of the emitted shock waves. In one embodiment the emitted shock waves are divergent or near planar. In another embodiment the emitted shock waves are convergent having a geometric focal volume of point at a distance of at least X from the source, the method further comprising positioning the tissue at a distance less than the distance X from the source. The tissue has cells. The tissue can be an organ of a mammal. The mammal may be a human or an animal. The organ may be a pancreas, a liver or a kidney or any other organ. The tissue preferably is part of the incretin system, including alpha cells, beta cells, neural or nerve cells and islets for insulin production, all in the pancreas. The step of subjecting the tissue to acoustic shock waves creates an analgesic effect on the nerve cells sufficient to initially deactivate the pancreatic sensory nerve cells and simultaneously stimulate the islets to begin producing insulin normally, this further reduces the chronic inflammation of the islets and can stimulate repair of damaged nerve cells to properly secrete neuropeptides thereby enabling the patient to be cured of the diabetic condition of type 1 or type 2 diabetes.

The method of stimulating a tissue can further include a result wherein the step of subjecting the tissue to acoustic shock waves stimulates at least some of said cells within said tissue to release or produce one or more of nitric oxygen (NO), vessel endothelial growth factor (VEGF), bone morphogenetic protein (BMP) or other growth factors.

In one method neuropeptide substance P can be directly injected into the pancreatic tissue and the shock wave used to stimulate the tissue.

The pancreatic tissue can have stem cells that are dormant or otherwise inactive, wherein the shock waves stimulate the stem cells with the treated tissue enhancing replications of the targeted tissue cells of the human or animal having such stem cells within the patient's body whether naturally occurring or artificially introduced which are activated or otherwise stimulated by the exposure to these shock waves.

In yet another embodiment the use of shock waves includes a method of preventive shock wave therapy having the steps of: identifying an at risk patient to diabetes having an at risk tissue; and subjecting the at risk tissue to shock waves to stimulate tissue repair. The step of identifying an at risk patient includes one or more indications of risk based on family history, genetic disposition, physical condition, or blood or tissue analysis. The method of preventive shock wave therapy further may have the step of testing the at risk tissue to establish measured baseline insulin production condition pre shock wave therapy and the step of post shock wave therapy testing the treated tissue for comparison to the baseline insulin production condition.

In each of these therapeutic methods or treatments using shock waves, the use or treatment may additionally include the use or administration of one or more antibiotics, drugs, chemicals, or other medical treatments to the blood stream or affected tissue cells stimulated by acoustic shock waves. The overall combination resulting in a reduced healing response time stimulated by the use of acoustic shock waves. In particular the antibiotics or other drugs that are introduced to the blood stream or affected tissue cells are beneficially assisted by the improved blood supply resulting from being stimulated by these acoustic shock waves. This means the drugs can work faster and be more efficient. The use of such acoustic waves in combination with antibiotics or other drugs means less potent or even lower dosages can be used in most treatments thereby lowering the risk of complications such as liver damage or the like.

The use of acoustic shock wave therapy is particularly important for diabetic patients having immune deficiency disorders such as those diagnosed with HIV or AIDs, the aged and smokers or those affected with emphysema.

DEFINITIONS

A "pressure pulse" according to the present invention is an acoustic pulse which includes several cycles of positive and negative pressure. The amplitude of the positive part of such a cycle should be above about 0.1 MPa and its time duration is from below a microsecond to about a second. Rise times of the positive part of the first pressure cycle may be in the range of nano-seconds (ns) up to some milli-seconds (ms). Very fast pressure pulses are called shock waves. Shock waves used in medical applications do have amplitudes above 0.1 MPa and rise times of the amplitude are below 100 ns. The duration of a shock wave is typically below 1-3 micro-seconds ($\mu$s) for the positive part of a cycle and typically above some microseconds for the negative part of a cycle.

A "paraboloid" according to the present invention is a three-dimensional reflecting bowl. In two dimensions (in Cartesian coordinates, x and y) the formula $y^2=2px$, wherein p/2 is the distance of the focal point of the paraboloid from its apex, defines the paraboloid. Rotation of the two-dimensional figure defined by this formula around its longitudinal axis generates a de facto paraboloid.

A "generalized paraboloid" according to the present invention is also a three-dimensional bowl. In two dimensions (in Cartesian coordinates, x and y) the formula $y^n=2px$ [with n being ≠2, but being greater than about 1.2 and smaller than 2, or greater than 2 but smaller than about 2.8]. In a generalized paraboloid, the characteristics of the wave fronts created by electrodes located within the generalized paraboloid may be corrected by the selection of (p(-z,+z)), with z being a measure for the burn down of an electrode, and n, so that phenomena including, but not limited to, burn down of the tip of an electrode (-z,+z) and/or disturbances caused by diffraction at the aperture of the paraboloid are compensated for.

Waves/wave fronts described as being "focused" or "having focusing characteristics" means in the context of the present invention that the respective waves or wave fronts are traveling and increase their amplitude in direction of the focal point. Per definition the energy of the wave will be at a maximum in the focal point or, if there is a focal shift in this point, the energy is at a maximum near the geometrical focal point. Both the maximum energy and the maximal pressure amplitude may be used to define the focal point.

"Divergent waves" in the context of the present invention are all waves which are not focused and are not plane or nearly plane. Divergent waves also include waves which only seem to have a focus or source from which the waves are transmitted. The wave fronts of divergent waves have divergent characteristics. Divergent waves can be created in many different way, for example: A focused wave will become divergent once it has passed through the focal point. Spherical waves are also included in this definition of divergent waves and have wave fronts with divergent characteristics.

"Plane waves" are sometimes also called flat or even waves. Their wave fronts have plane characteristics (also called even or parallel characteristics). The amplitude in a wave front is constant and the "curvature" is flat (that is why these waves are sometimes called flat waves). Plane waves do not have a focus to which their fronts move (focused) or from which the fronts are emitted (divergent). "Nearly plane waves" also do not have a focus to which their fronts move (focused) or from which the fronts are emitted (divergent). The amplitude of their wave fronts (having "nearly plane" characteristics) is approximating the constancy of plain waves. "Nearly plane" waves can be emitted by generators having pressure pulse/shock wave generating elements with flat emitters or curved emitters. Curved emitters may comprise a generalized paraboloid that allows waves having nearly plane characteristics to be emitted.

A "curved emitter" is an emitter having a curved reflecting (or focusing) or emitting surface and includes, but is not limited to, emitters having ellipsoidal, parabolic, quasi parabolic (general paraboloid) or spherical reflector/reflecting or emitting elements. Curved emitters having a curved reflecting or focusing element generally produce waves having focused wave fronts, while curved emitters having a curved emitting surfaces generally produce wave having divergent wave fronts.

"AIDS" An acquired defect of cellular immunity associated with infection by the human immunodeficiency virus (HIV), a CD4-positive T-lymphocyte count under 200 cells/microliter or less than 14% of total lymphocytes, and increased susceptibility to opportunistic infections and malignant neoplasms. Clinical manifestations also include emaciation (wasting) and dementia. These elements reflect criteria for AIDS as defined by the CDC in 1993.

"Crohn's disease" (also known as regional enteritis) is a chronic, episodic, inflammatory condition of the gastrointestinal tract characterized by transmural inflammation (affecting the entire wall of the involved bowel) and skip lesions (areas of inflammation with areas of normal lining in between). Crohn's disease is a type of inflammatory bowel disease (IBD) and can affect any part of the gastrointestinal tract from mouth to anus; as a result, the symptoms of Crohn's disease can vary between affected individuals. The main gastrointestinal symptoms are abdominal pain, diarrhea, which may be bloody, and weight loss. Crohn's disease can also cause complications outside of the gastrointestinal tract such as skin rashes, arthritis, and inflammation of the eye.

"diabetes" A heterogeneous group of disorders that share glucose intolerance in common.

"HIV" Human immunodeficiency virus. Species of LENTIVIRUS, subgenus primate lentiviruses (LENTIVIRUSES, PRIMATE), formerly designated T-cell lymphotropic virus type III/lymphadenopathy-associated virus (HTLV-III/LAV). It is acknowledged to be the agent responsible for the acute infectious manifestations, neurologic disorders, and immunologic abnormalities linked to the ACQUIRED IMMUNO-DEFICIENCY SYNDROME.

BRIEF DESCRIPTION OF THE DRAWINGS

The invention will be described by way of example and with reference to the accompanying drawings in which.

DETAILED DESCRIPTION OF THE INVENTION

Figure 1:
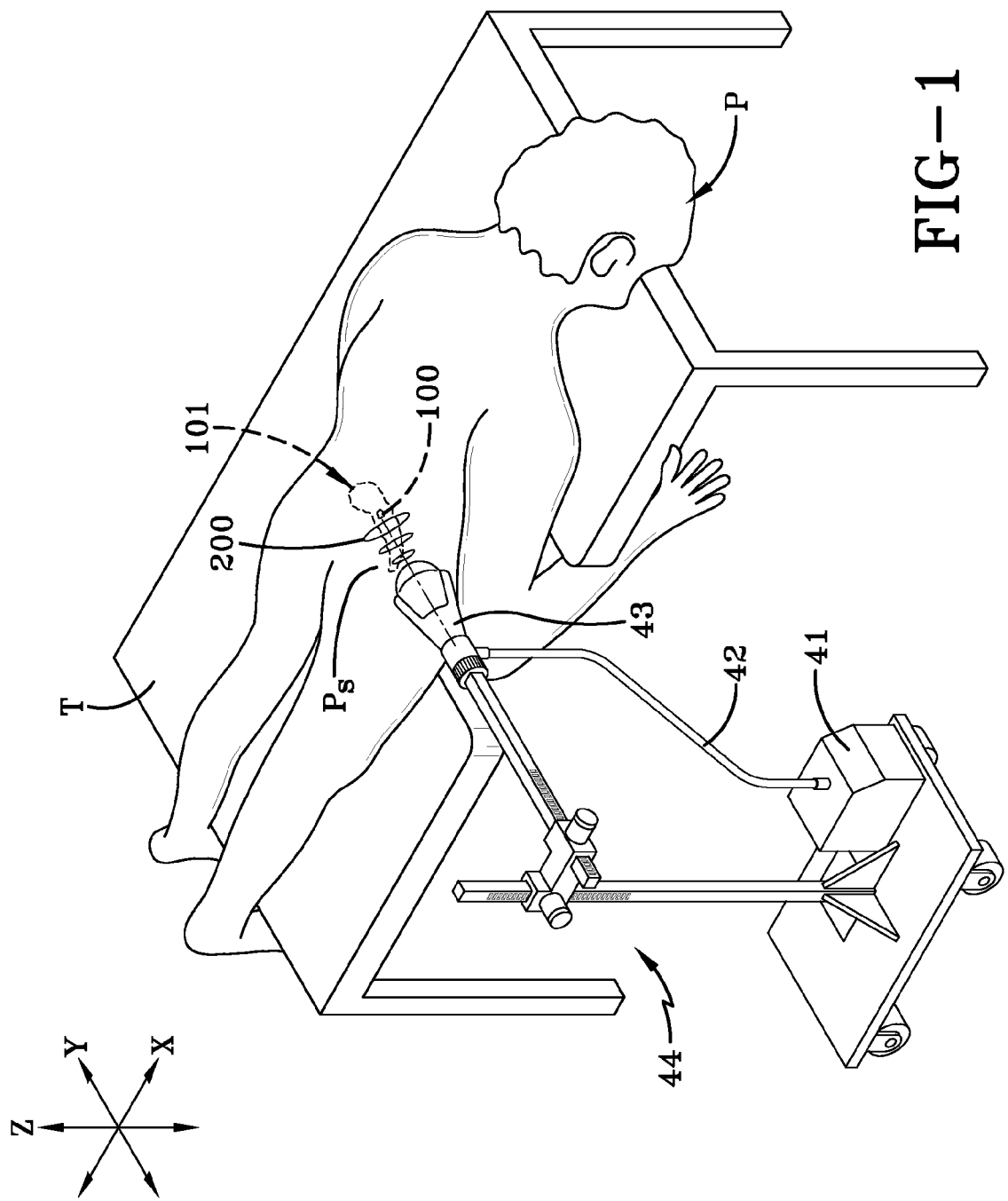
FIG. 1 illustrates a diabetic patient or a patient at risk of diabetes being treated with a shock wave apparatus in the region of the pancreas, the patient being oriented face down and lying on his stomach.

With reference to FIG. 1, the patient P who has either been diagnosed with diabetes or is at risk of contracting diabetes is positioned on a table T preferably face down lying on the stomach. A shock wave applicator head 43 is brought into contact with the skin $P_s$ preferably an acoustic gel is used to enhance the transmission of the shock waves 200 through the body down to the subsurface tissue 100 of the pancreas 101. The shock wave applicator head 43 is connected via cabling 42 to a power generating unit 41 as shown. The shock wave applicator head 43 can be attached rigidly to a fixture or stand 44 as illustrated or alternatively can be hand held and manipulated across the skin $P_s$ to drive the shock waves 200 in the direction the shock wave head 43 is pointed.

Figure 2:
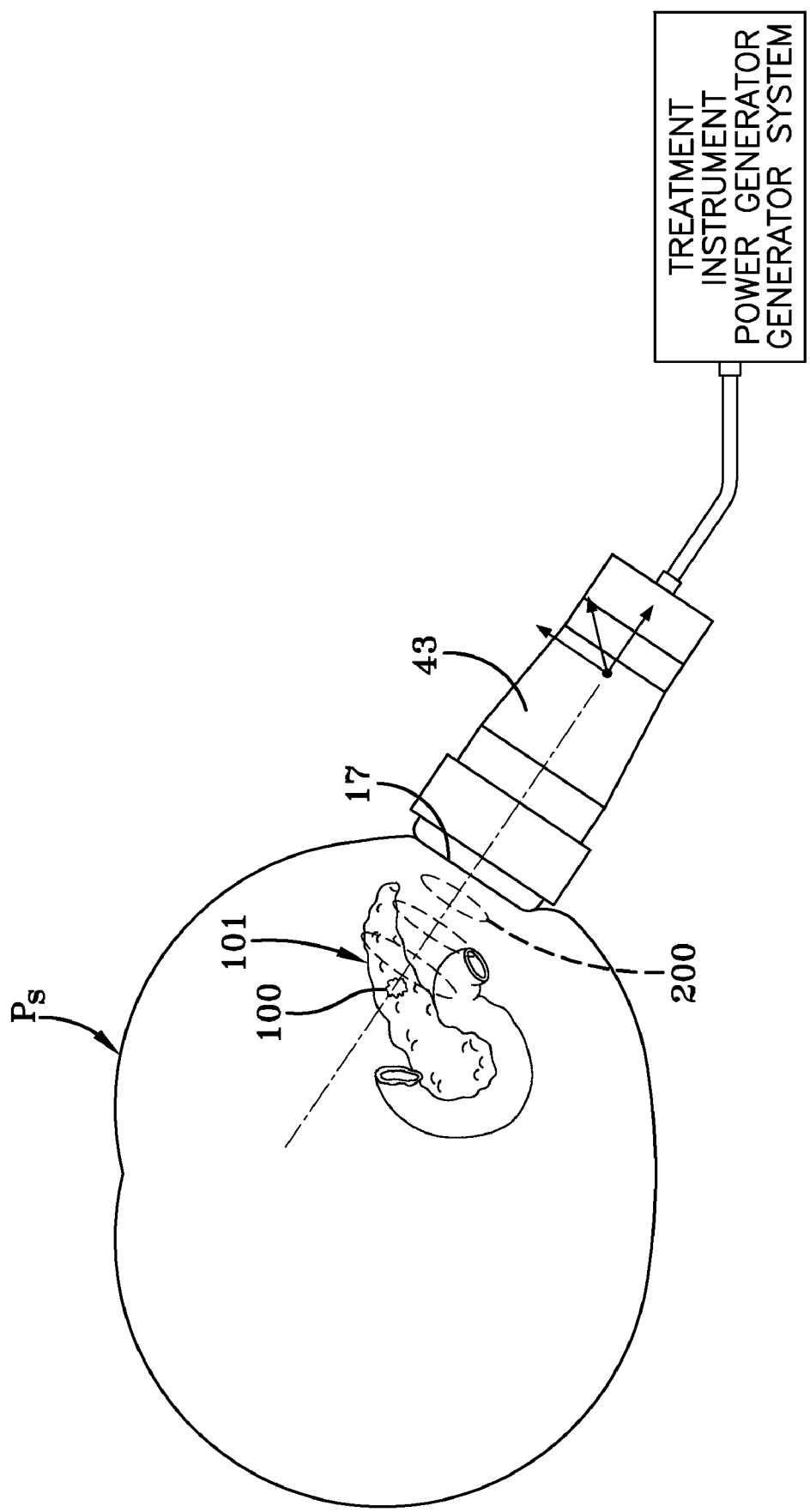
FIG. 2 an enlarged view of the pancreatic region of the patient is shown wherein the shock wave head is shown in proximity to the pancreas and is shown emitting shock waves throughout the pancreatic tissue.

With reference to FIG. 2 an enlarged portion of the patient P's body is shown directly above the region of the pancreas 101. As illustrated the pancreas 101 is being bombarded with shock waves 200 that are emitted from the lens 17 directly into the patient P to provide the therapeutic treatment of acoustic shock waves 200 to the subsurface tissue 100.

Figure 3:
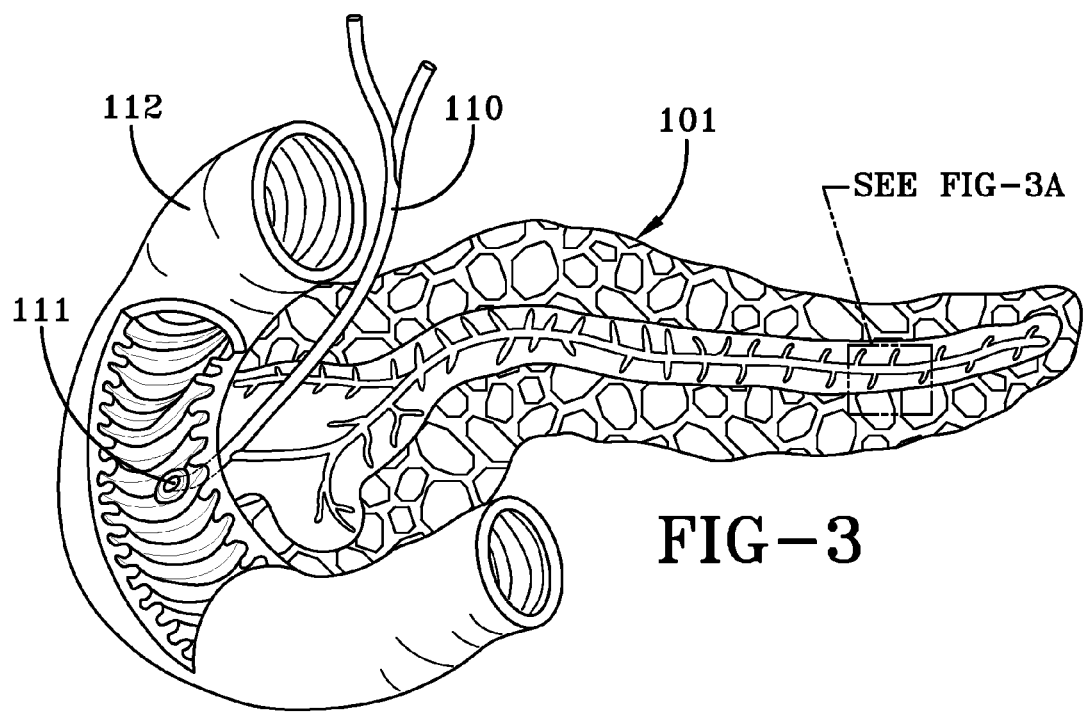
FIG. 3 is a view of the portion of the pancreas connected via the pancreatic duct entering the duodenum.
Figure 3A:
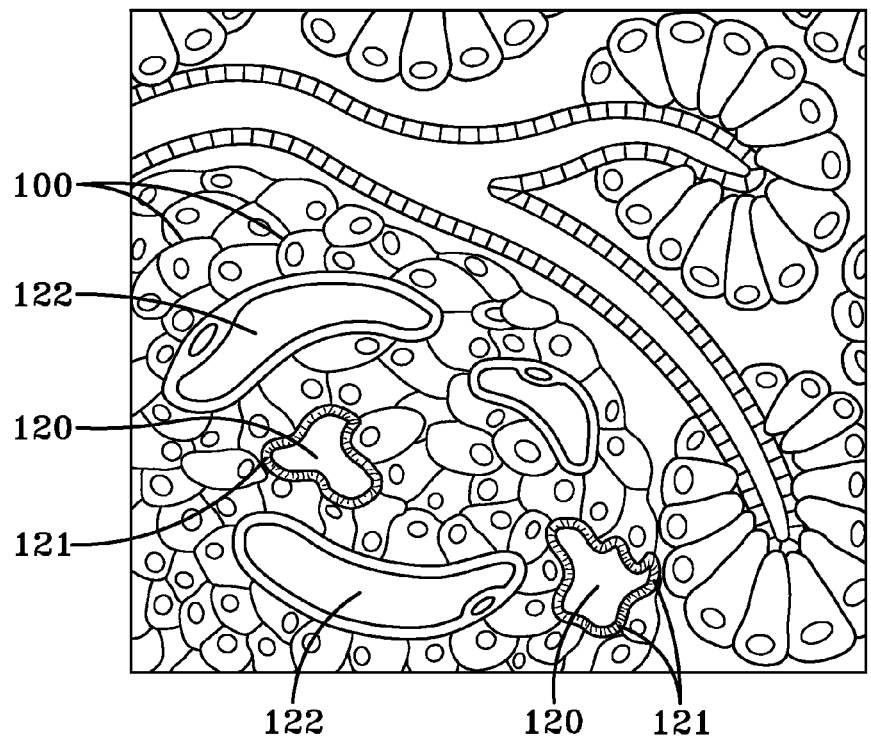
FIG. 3A is an enlarged section of tissue taken from the pancreas of FIG. 3 to illustrate the islets and surrounding nerves.

With reference to FIG. 3 an enlarged view of the pancreas 101 is shown along with the connecting tissue of the bile duct 110 connected from the liver and from the gall bladder (not illustrated) and a portion of the duodenum 112 from the stomach as it extends to the small bowel (also not illustrated). The pancreatic duct 111 enters the duodenum 112 as illustrated. The tissue 100 of the pancreas 101 as further illustrated in FIG. 3A has islets 120 that are surrounded by a large number of nerve cells 121 illustrated as hair like features.

These islets 120 are used in the production of insulin and then nerve cells 121 surrounding the islets play an important role in the proper functioning of the pancreas 101. Numerous large blood vessels 122 like within the pancreatic tissue 100. When these nerve cells 121 are irritated or not properly producing neuropeptides, it is possible to shut down the islets 120 such that they will no longer properly produce insulin. This is a condition commonly referred to as diabetes and can occur in type 1 or type 2 diabetes. When this condition occurs, it has been determined that shutting the nerve cells 121 down for a period of time will enable the islets 120 to continue to produce insulin in a normal fashion. It has therefore been determined that the analgesic effect of shock waves 200 when bombarding the pancreas 101 can be used to deactivate the nerve cells 121 surrounding the islet 120 such that these islets can begin to produce insulin properly. After a treatment with shock waves 200 it has further been determined that the damaged nerve cells 121 in the incretin nerve system surrounding the islets 120 can be healed and stimulated to properly secrete neuropeptides which when properly secreted further enhance the ability of the islets to produce insulin normally. After treatment with shock waves 200 the chronic inflammation commonly associated with the pancreas and these tissues 100 can be reduced dramatically indicating that the tissue 100 is now healed in such a fashion that the nerves 121 surrounding the islets 120 are no longer irritated or sensitized and that the entire pancreatic system can now perform properly. As indicated it is possible to inject neuropeptide substance P directly into the tissue 100 and then stimulate the pancreatic subsurface tissue 100 by the use of therapeutic treatment of acoustic shock waves 200. The common pain associated with the pancreatic condition can be alleviated in this way and the proper functioning of the pancreas 101 can be stimulated such that the diabetic condition can be eliminated or greatly reduced and the pancreas 101 can operate normally producing insulin that the body will accept. This condition can be conducted on a person already experiencing diabetic indications of type 1 or type 2 or can be used on people with known risk of diabetic conditions. It is preferred that the treatment be used with non focused shock waves to eliminate or minimize hemorrhaging or focused shock waves can be used wherein the wave pattern does not have the focal point generated on the pancreatic tissue 100, otherwise this can create hemorrhaging and potential damage to the pancreas 101 if the intensity level of the focused shock wave is too intense. For these reasons it is preferable to use the divergent or non-planar or planar shock waves for the treatment of a diabetic pancreas 101. These lower energy, lower amplitude shock waves described hereinafter can provide the beneficial effects without creating any trauma to the pancreas, furthermore these treatments can be done on an outpatient basis as will be described.

The following description of the proper amplitude and pressure pulse intensities of the shock waves 200 are provided below along with a description of how the shock waves actually function and have been taken from the co-pending application of the present inventors and replicated herein as described below. For the purpose of describing the shock waves 200 were used as exemplary and are intended to include all of the wave patterns discussed in FIGS. 4A-15 as possible treatment patterns.

This method of treatment has the steps of, locating a treatment site, generating either convergent diffused or far-sighted focused shock waves or unfocused shock waves, of directing these shock waves to the treatment site; and applying a sufficient number of these shock waves to induce activation of one or more growth factor thereby inducing or accelerating healing.

The unfocused shock waves can be of a divergent wave pattern or near planar pattern preferably of a low peak pressure amplitude and density. Typically the energy density values range as low as 0.000001 $mJ/mm^2$ and having a high end energy density of below 1.0 $mJ/mm^2$, preferably 0.20 $mJ/mm^2$ or less. The peak pressure amplitude of the positive part of the cycle should be above 1.0 and its duration is below 1-3 microseconds.

The treatment depth can vary from the surface to the full depth of the human or animal torso and the treatment site can be defined by a much larger treatment area than the 0.10-3.0 $cm^2$ commonly produced by focused waves. The above methodology is particularly well suited for surface as well as sub-surface soft tissue treatments.

While one of the benefits of the non-invasive nature of this treatment relates to reducing patient recovery and healing time, the fact that the treatments can be delivered at dosages well below the threshold of pain means that no local or general anesthesia is typically required as a consequence of the treatment. This alone significantly reduces any risk factors or complications associated with pain management during the procedure. The treatments further can reduce the need for a regiment of chemical or drug therapies before or after exposure to this shock wave therapy. Alternatively, ESWT can be used in conjunction with chemical or drug therapies to increase the cellular response permitting an opportunity to lower dosages of such chemicals or drugs while increasing the therapeutic efficiency. This is a particularly useful tool for the physician whose patient is elderly, a smoker or with an immune system deficiency which would complicate if not make unavailable more traditional invasive surgical procedures. In fact the above methodology proposed in this patent may be the first if not only choice of treatment available for patients in this class wherein heretofore conventional procedures were deemed too risky.

A further clinical benefit of the above methodology is that the procedure can be done either as an outpatient treatment or at a doctor's office assuming the patient's condition does not otherwise require hospitalization.

The stimulation of growth factors and activation of healing acceleration is particularly valuable to elderly patients and other high risk factor subjects.

Even more striking as mentioned earlier, early prevention therapies can be employed to stimulate tissue or organ modeling to be maintained within acceptable ranges prior to a degeneration occurring. This is extremely valuable in the prevention of diabetes or heart disease for example. The methods would be to identify at risk patients based on family history or genetic disposition, physical condition, etc. and subjecting that patient to therapeutic shock wave therapy for the purpose of stimulating tissue repair effectively remodeling the patient's susceptible organ to be within accepted functional parameters. The objective being to preventively stimulate cellular tissue repairs to preemptively avoid a degenerative condition from occurring which may require invasive surgical procedures.

Figure 4A:
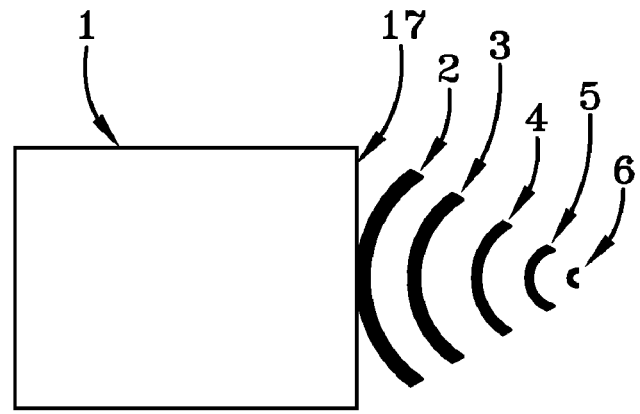
FIG. 4A is a simplified depiction of a pressure pulse/shock wave (PP/SW) generator with focusing wave characteristics.

FIG. 4A is a simplified depiction of the a pressure pulse/shock wave (PP/SW) generator, such as a shock wave head, showing focusing characteristics of transmitted acoustic pressure pulses. Numeral 1 indicates the position of a generalized pressure pulse generator, which generates the pressure pulse and, via a focusing element, focuses it outside the housing to treat diseases. The diseased organ is generally located in or near the focal point which is located in or near position 6. At position 17 a water cushion or any other kind of exit window for the acoustical energy is located.

Figure 4B:
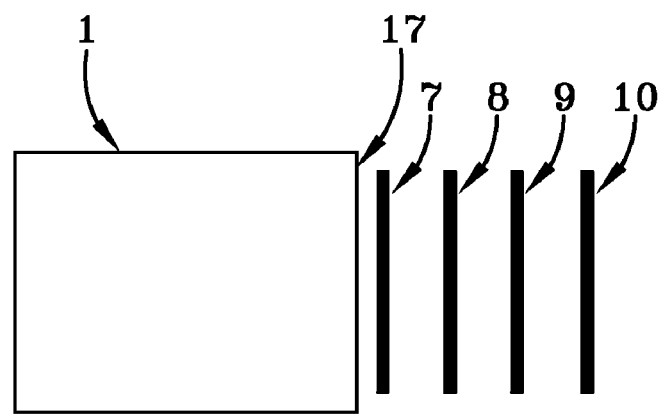
FIG. 4B is a simplified depiction of a pressure pulse/shock wave generator with plane wave characteristics.

FIG. 4B is a simplified depiction of a pressure pulse/shock wave generator, such as a shock wave head, with plane wave characteristics. Numeral 1 indicates the position of a pressure pulse generator according to the present invention, which generates a pressure pulse which is leaving the housing at the position 17, which may be a water cushion or any other kind of exit window. Somewhat even (also referred to herein as "disturbed") wave characteristics can be generated, in case a paraboloid is used as a reflecting element, with a point source (e.g. electrode) that is located in the focal point of the paraboloid. The waves will be transmitted into the patient's body via a coupling media such as, e.g., ultrasound gel or oil and their amplitudes will be attenuated with increasing distance from the exit window 17.

Figure 4C:
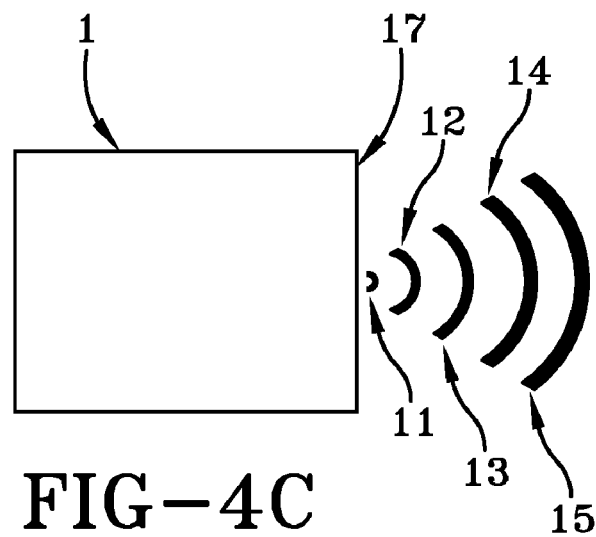
FIG. 4C is a simplified depiction of a pressure pulse/shock wave generator with divergent wave characteristics.

FIG. 4C is a simplified depiction of a pressure pulse shock wave generator (shock wave head) with divergent wave characteristics. The divergent wave fronts may be leaving the exit window 17 at point 11 where the amplitude of the wave front is very high. This point 17 could be regarded as the source point for the pressure pulses. In FIG. 4C the pressure pulse source may be a point source, that is, the pressure pulse may be generated by an electrical discharge of an electrode under water between electrode tips. However, the pressure pulse may also be generated, for example, by an explosion. The divergent characteristics of the wave front may be a consequence of the mechanical setup shown in FIG. 5B.

Figure 5A:
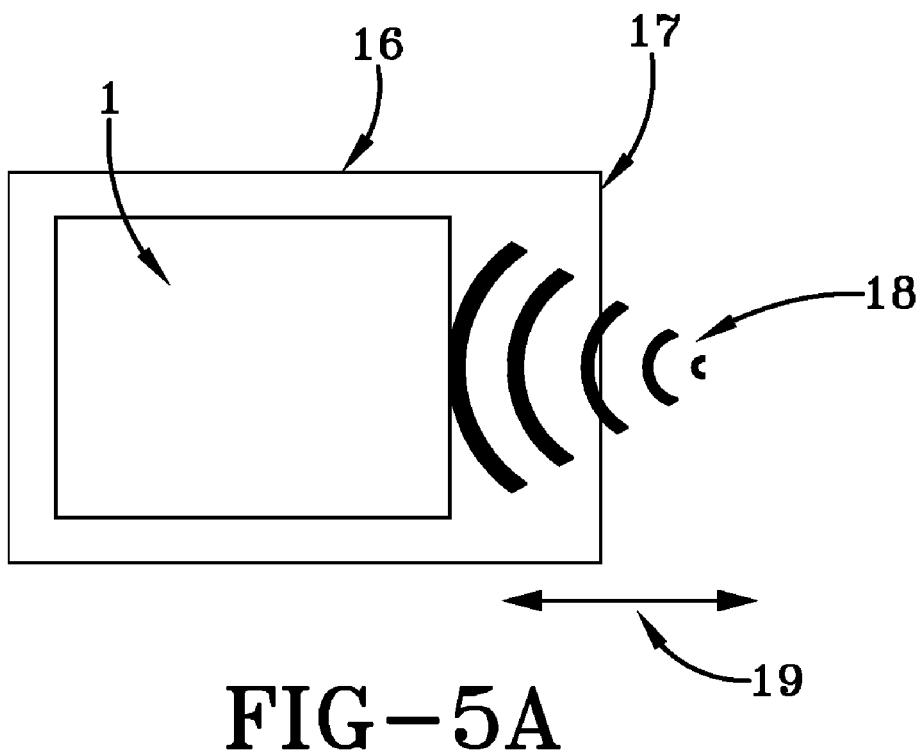
FIG. 5A is a simplified depiction of a pressure pulse/shock wave generator having an adjustable exit window along the pressure wave path. The exit window is shown in a focusing position.

FIG. 5A is a simplified depiction of a pressure pulse/shock wave generator (shock wave head) according to the present invention having an adjustable or exchangeable (collectively referred to herein as "movable") housing around the pressure wave path. The apparatus is shown in a focusing position. FIG. 5A is similar to FIG. 4A but depicts an outer housing (16) in which the acoustical pathway (pressure wave path) is located. In a preferred embodiment, this pathway is defined by especially treated water (for example, temperature controlled, conductivity and gas content adjusted water) and is within a water cushion or within a housing having a permeable membrane, which is acoustically favorable for the transmission of the acoustical pulses. In certain embodiments, a complete outer housing (16) around the pressure pulse/shock wave generator (1) may be adjusted by moving this housing (16) in relation to, e.g., the focusing element in the generator. However, as the person skilled in the art will appreciate, this is only one of many embodiments of the present invention. While the figure shows that the exit window (17) may be adjusted by a movement of the complete housing (16) relative to the focusing element, it is clear that a similar, if not the same, effect can be achieved by only moving the exit window, or, in the case of a water cushion, by filling more water in the volume between the focusing element and the cushion. FIG. 5A shows the situation in which the arrangement transmits focused pressure pulses.

Figure 5B:
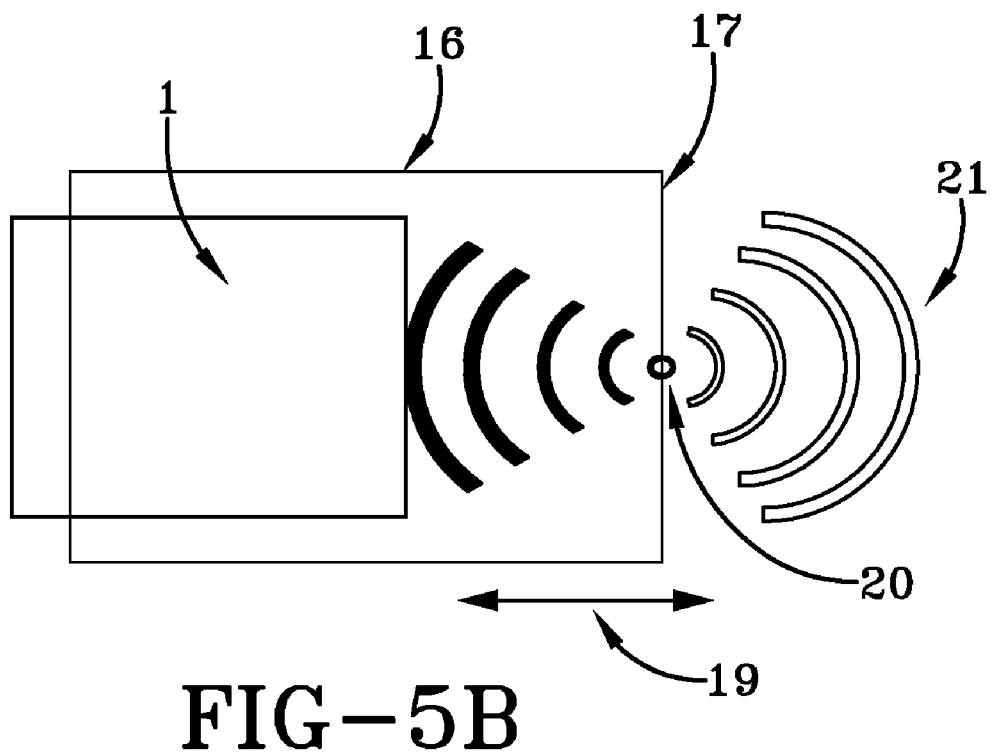
FIG. 5B is a simplified depiction of a pressure pulse/shock wave generator having an exit window along the pressure wave path. The exit window as shown is positioned at the highest energy divergent position.

FIG. 5B is a simplified depiction of the pressure pulse/shock wave generator (shock wave head) having an adjustable or exchangeable housing around the pressure wave path with the exit window 17 being in the highest energy divergent position. The configuration shown in FIG. 5B can, for example, be generated by moving the housing (16) including the exit window (17), or only the exit window (17) of a water cushion, towards the right (as shown in the Figure) to the second focus f2 (20) of the acoustic waves. In a preferred embodiment, the energy at the exit window will be maximal. Behind the focal point, the waves may be moving with divergent characteristics (21).

Figure 5C:
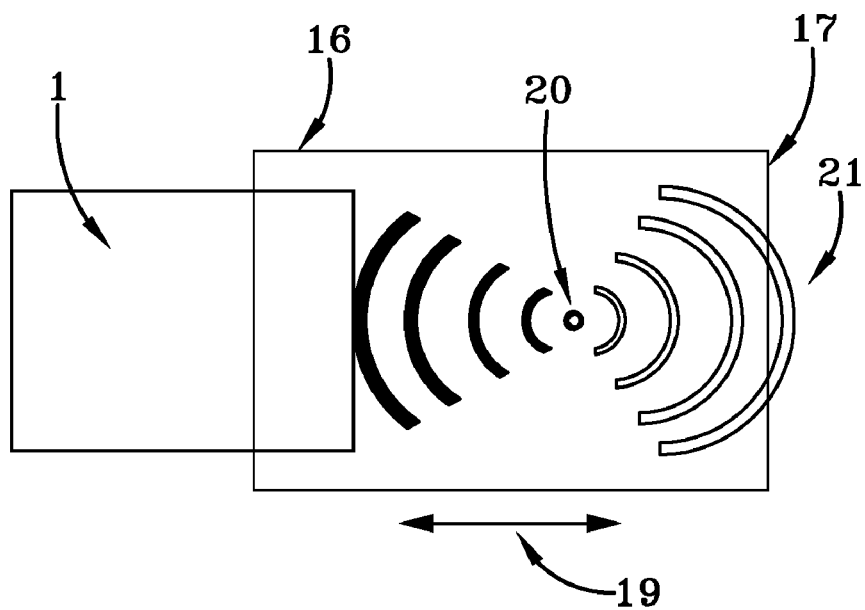
FIG. 5C is a simplified depiction of a pressure pulse/shock wave generator having an exit window along the pressure wave path. The exit window is shown at a low energy divergent position.

FIG. 5C is a simplified depiction of the pressure pulse/shock wave generator (shock wave head) having an adjustable or exchangeable housing around the pressure wave path in a low energy divergent position. The adjustable housing or water cushion is moved or expanded much beyond f2 position (20) so that highly divergent wave fronts with low energy density values are leaving the exit window (17) and may be coupled to a patient's body. Thus, an appropriate adjustment can change the energy density of a wave front without changing its characteristic.

This apparatus may, in certain embodiments, be adjusted/modified/or the complete shock wave head or part of it may be exchanged so that the desired and/or optimal acoustic profile such as one having wave fronts with focused, nearly plane or divergent characteristics can be chosen.

A change of the wave front characteristics may, for example, be achieved by changing the distance of the exit acoustic window relative to the reflector, by changing the reflector geometry, by introducing certain lenses or by removing elements such as lenses that modify the waves produced by a pressure pulse/shock wave generating element. Exemplary pressure pulse/shock wave sources that can, for example, be exchanged for each other to allow an apparatus to generate waves having different wave front characteristics are described in detail below.

In certain embodiments, the change of the distance of the exit acoustic window can be accomplished by a sliding movement. However, in other embodiments of the present invention, in particular, if mechanical complex arrangements, the movement can be an exchange of mechanical elements.

In one embodiment, mechanical elements that are exchanged to achieve a change in wave front characteristics include the primary pressure pulse generating element, the focusing element, the reflecting element, the housing and the membrane. In another embodiment, the mechanical elements further include a closed fluid volume within the housing in which the pressure pulse is formed and transmitted through the exit window.

In one embodiment, the apparatus of the present invention is used in combination therapy. Here, the characteristics of waves emitted by the apparatus are switched from, for example, focused to divergent or from divergent with lower energy density to divergent with higher energy density. Thus, effects of a pressure pulse treatment can be optimized by using waves having different characteristics and/or energy densities, respectively.

While the above described universal toolbox of the present invention provides versatility, the person skilled in the art will appreciate that apparatuses that only produce waves having, for example, nearly plane characteristics, are less mechanically demanding and fulfill the requirements of many users.

As the person skilled in the art will also appreciate that embodiments shown in drawings 4A-4C and 5A-5C are independent of the generation principle and thus are valid for not only electro-hydraulic shock wave generation but also for, but not limited to, PP/SW generation based on electromagnetic, piezoceramic and ballistic principles. The pressure pulse generators may, in certain embodiments, be equipped with a water cushion that houses water which defines the path of pressure pulse waves that is, through which those waves are transmitted. In a preferred embodiment, a patient is coupled via ultrasound gel or oil to the acoustic exit window (17), which can, for example, be an acoustic transparent membrane, a water cushion, a plastic plate or a metal plate.

Figure 6:
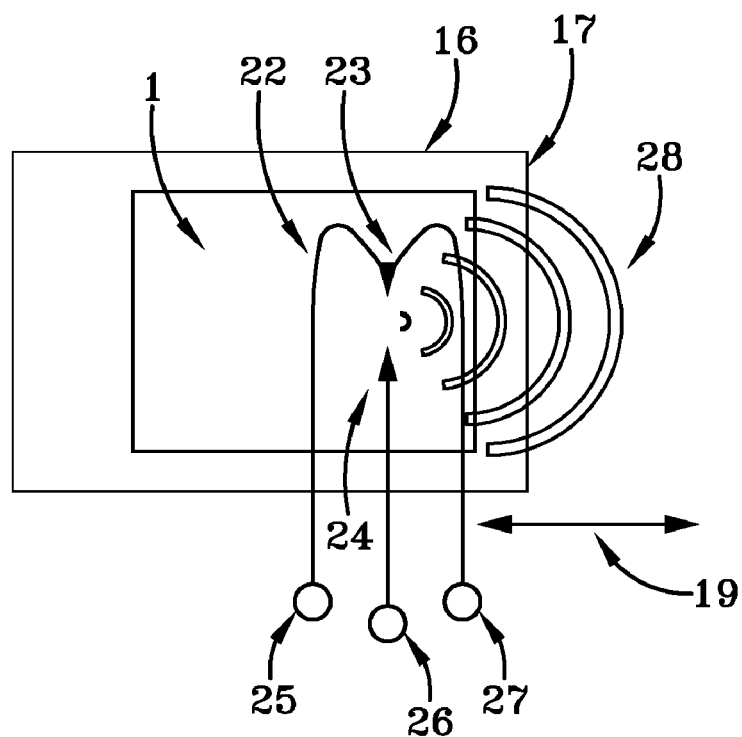
FIG. 6 is a simplified depiction of an electro-hydraulic pressure pulse/shock wave generator having no reflector or focusing element. Thus, the waves of the generator did not pass through a focusing element prior to exiting it.

FIG. 6 is a simplified depiction of the pressure pulse/shock wave apparatus having no focusing reflector or other focusing element. The generated waves emanate from the apparatus without coming into contact with any focusing elements. FIG. 6 shows, as an example, an electrode as a pressure pulse generating element producing divergent waves (28) behind the ignition point defined by a spark between the tips of the electrode (23, 24).

Figure 7A:
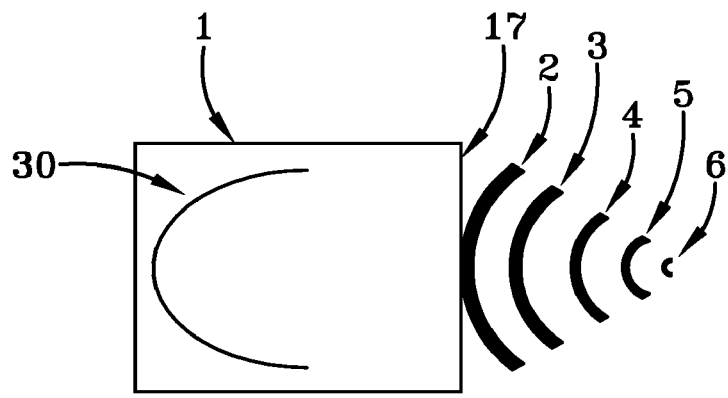
FIG. 7A is a simplified depiction of a pressure pulse/shock wave generator having a focusing element in the form of an ellipsoid. The waves generated are focused.

FIG. 7A is a simplified depiction of the pressure pulse/shock wave generator (shock wave head) having as focusing element an ellipsoid (30). Thus, the generated waves are focused at (6).

Figure 7B:
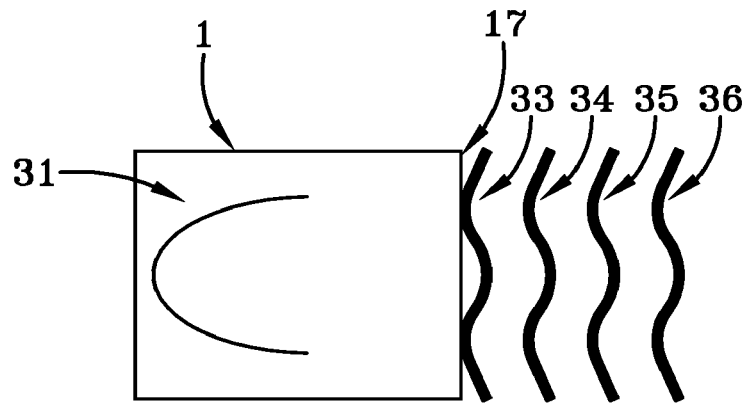
FIG. 7B is a simplified depiction of a pressure pulse/shock wave generator having a parabolic reflector element and generating waves that are disturbed plane.

FIG. 7B is a simplified depiction of the pressure pulse/shock wave generator (shock wave head) having as a focusing element an paraboloid ($y^2=2px$). Thus, the characteristics of the wave fronts generated behind the exit window (33, 34, 35, and 36) are disturbed plane ("parallel"), the disturbance resulting from phenomena ranging from electrode burn down, spark ignition spatial variation to diffraction effects. However, other phenomena might contribute to the disturbance.

Figure 7C:
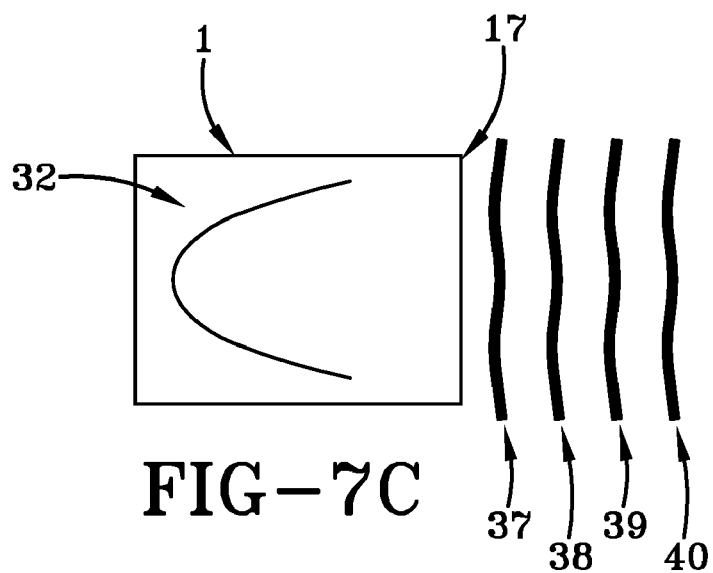
FIG. 7C is a simplified depiction of a pressure pulse/shock wave generator having a quasi parabolic reflector element (generalized paraboloid) and generating waves that are nearly plane/have nearly plane characteristics.

FIG. 7C is a simplified depiction of the pressure pulse/shock wave generator (shock wave head) having as a focusing element a generalized paraboloid ($y^n=2px$, with $1.2 \leq n \leq 2.8$ and $n \neq 2$). Thus, the characteristics of the wave fronts generated behind the exit window (37, 38, 39, and 40) are, compared to the wave fronts generated by a paraboloid ($y^2=2px$), less disturbed, that is, nearly plane (or nearly parallel or nearly even (37, 38, 39, 40)). Thus, conformational adjustments of a regular paraboloid ($y^2=2px$) to produce a generalized paraboloid can compensate for disturbances from, e.g., electrode burn down. Thus, in a generalized paraboloid, the characteristics of the wave front may be nearly plane due to its ability to compensate for phenomena including, but not limited to, burn down of the tips of the electrode and/or for disturbances caused by diffraction at the aperture of the paraboloid. For example, in a regular paraboloid ($y^2=2px$) with p=1.25, introduction of a new electrode may result in p being about 1.05. If an electrode is used that adjusts itself to maintain the distance between the electrode tips ("adjustable electrode") and assuming that the electrodes burn down is 4 mm (z=4 mm), p will increase to about 1.45. To compensate for this burn down, and here the change of p, and to generate nearly plane wave fronts over the life span of an electrode, a generalized paraboloid having, for example n=1.66 or n=2.5 may be used. An adjustable electrode is, for example, disclosed in U.S. Pat. No. 6,217,531.

Figure 7D:
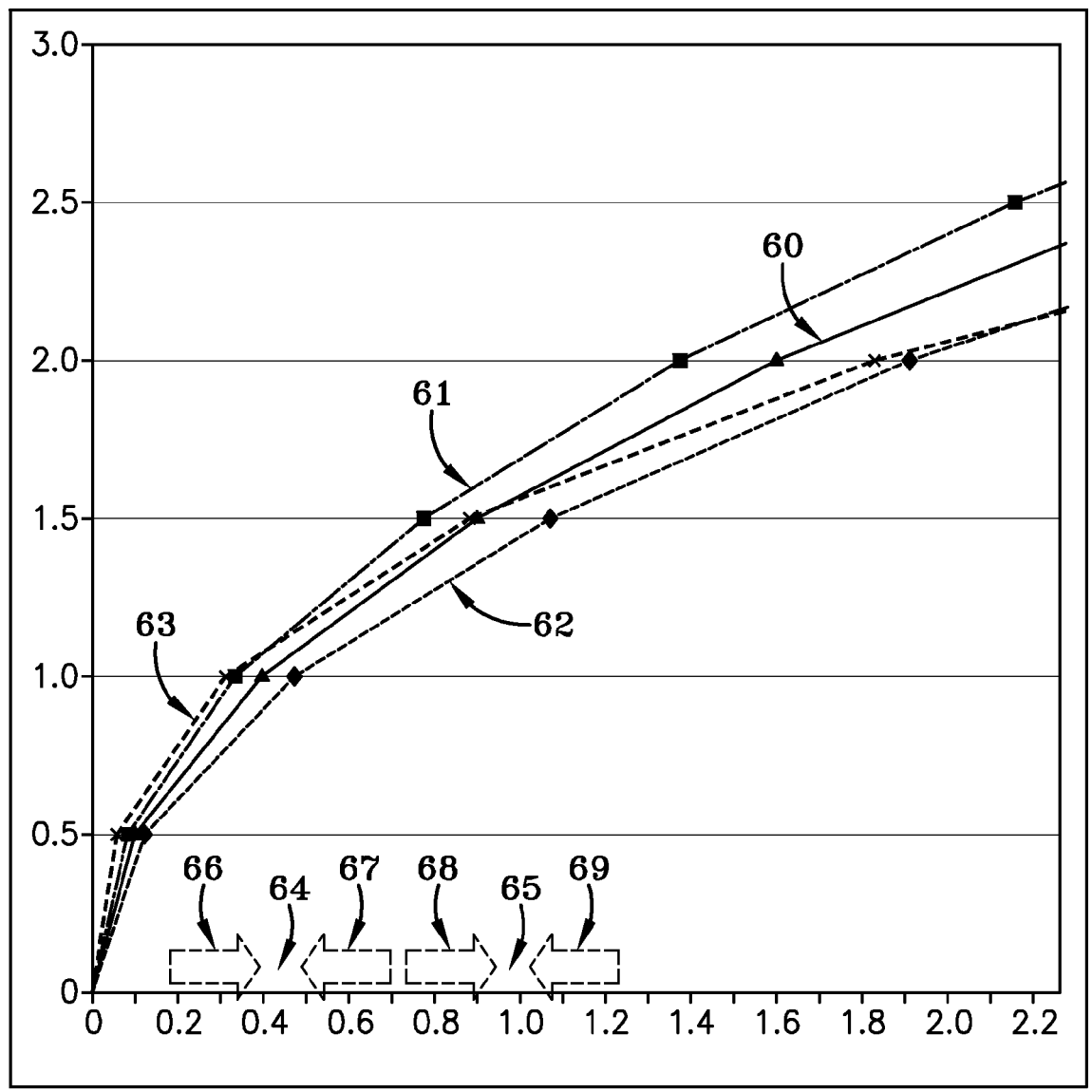
FIG. 7D is a simplified depiction of a generalized paraboloid with better focusing characteristic than a paraboloid in which n=2. The electrode usage is shown. The generalized paraboloid, which is an interpolation (optimization) between two optimized paraboloids for a new electrode and for a used (burned down) electrode is also shown.

FIG. 7D shows sectional views of a number of paraboloids. Numeral 62 indicates a paraboloid of the shape $y^2=2px$ with p=0.9 as indicated by numeral 64 at the x axis which specifies the p/2 value (focal point of the paraboloid). Two electrode tips of a new electrode 66 (inner tip) and 67 (outer tip) are also shown in the Figure. If the electrodes are fired and the tips are burning down the position of the tips change, for example, to position 68 and 69 when using an electrode which adjusts its position to compensate for the tip burn down. In order to generate pressure pulse/shock waves having nearly plane characteristics, the paraboloid has to be corrected in its p value. The p value for the burned down electrode is indicate by 65 as p/2=1. This value, which constitutes a slight exaggeration, was chosen to allow for an easier interpretation of the Figure. The corresponding paraboloid has the shape indicated by 61, which is wider than paraboloid 62 because the value of p is increased. An average paraboloid is indicated by numeral 60 in which p=1.25 cm. A generalized paraboloid is indicated by dashed line 63 and constitutes a paraboloid having a shape between paraboloids 61 and 62. This particular generalized paraboloid was generated by choosing a value of $n \neq 2$ and a p value of about 1.55 cm. The generalized paraboloid compensates for different p values that result from the electrode burn down and/or adjustment of the electrode tips.

Figure 8:
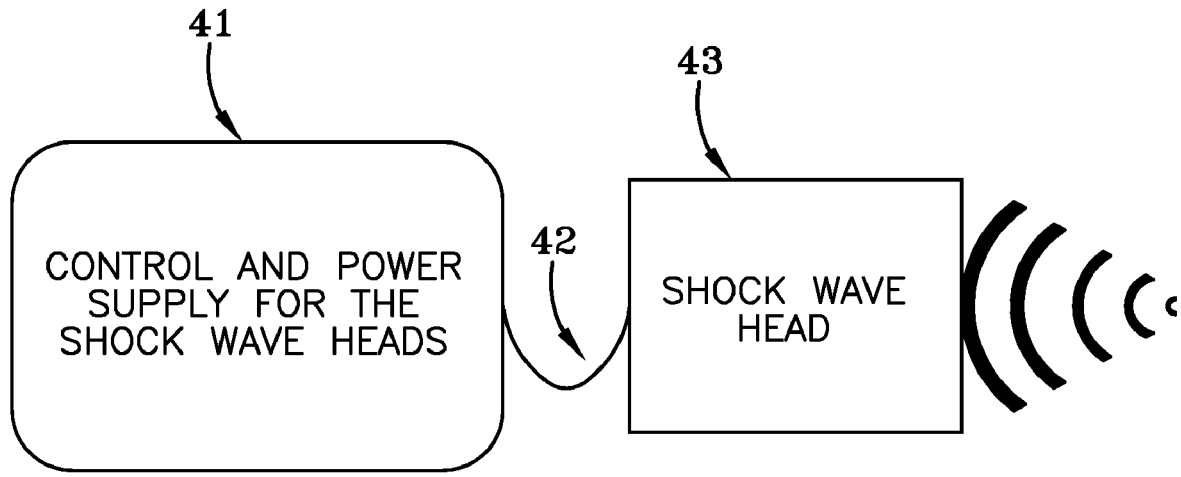
FIG. 8 is a simplified depiction of a pressure pulse/shock wave generator being connected to a control/power supply unit.

FIG. 8 is a simplified depiction of a set-up of the pressure pulse/shock wave generator (43) (shock wave head) and a control and power supply unit (41) for the shock wave head (43) connected via electrical cables (42) which may also include water hoses that can be used in the context of the present invention. However, as the person skilled in the art will appreciate, other set-ups are possible and within the scope of the present invention.

Figure 9:
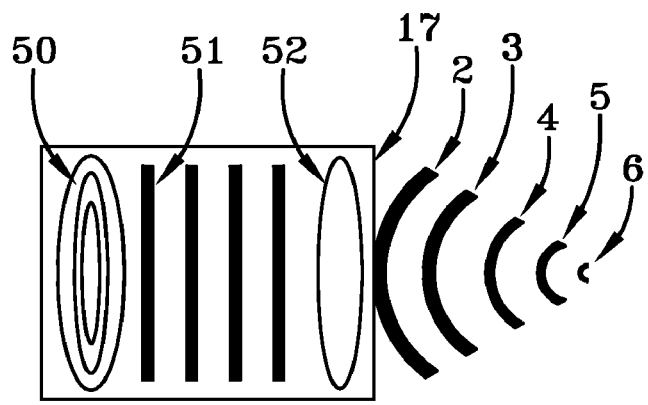
FIG. 9 is a simplified depiction of a pressure pulse/shock wave generator comprising a flat EMSE (electromagnetic shock wave emitter) coil system to generate nearly plane waves as well as an acoustic lens. Convergent wave fronts are leaving the housing via an exit window.

FIG. 9 is a simplified depiction of the pressure pulse/shock wave generator (shock wave head) having an electromagnetic flat coil 50 as the generating element. Because of the plane surface of the accelerated metal membrane of this pressure pulse/shock wave generating element, it emits nearly plane waves which are indicated by lines 51. In shock wave heads, an acoustic lens 52 is generally used to focus these waves. The shape of the lens might vary according to the sound velocity of the material it is made of. At the exit window 17 the focused waves emanate from the housing and converge towards focal point 6.

Figure 10:
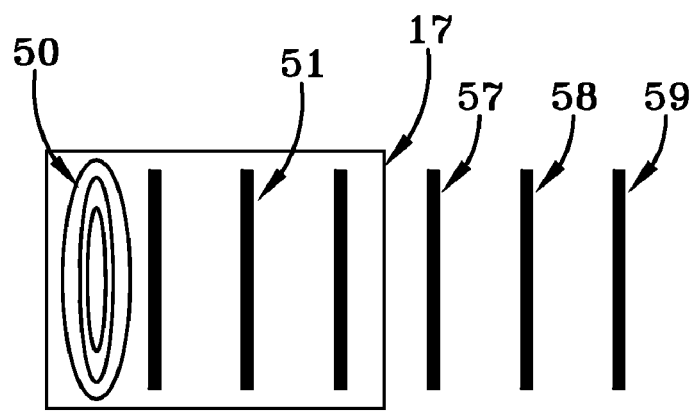
FIG. 10 is a simplified depiction of a pressure pulse/shock wave generator having a flat EMSE coil system to generate nearly plane waves. The generator has no reflecting or focusing element. As a result, the pressure pulse/shock waves are leaving the housing via the exit window unfocused having nearly plane wave characteristics.

FIG. 10 is a simplified depiction of the pressure pulse/shock wave generator (shock wave head) having an electromagnetic flat coil 50 as the generating element. Because of the plane surface of the accelerated metal membrane of this generating element, it emits nearly plane waves which are indicated by lines 51. No focusing lens or reflecting lens is used to modify the characteristics of the wave fronts of these waves, thus nearly plane waves having nearly plane characteristics are leaving the housing at exit window 17.

Figure 11:
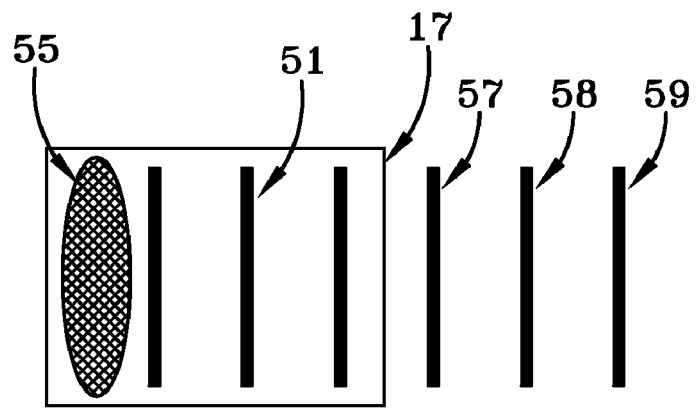
FIG. 11 is a simplified depiction of a pressure pulse/shock wave generator having a flat piezoceramic plate equipped with a single or numerous individual piezoceramic elements to generate plane waves without a reflecting or focusing element. As a result, the pressure pulse/shock waves are leaving the housing via the exit window unfocused having nearly plane wave characteristics.

FIG. 11 is a simplified depiction of the pressure pulse/shock wave generator (shock wave head) having an piezoceramic flat surface with piezo crystals 55 as the generating element. Because of the plane surface of this generating element, it emits nearly plane waves which are indicated by lines 51. No focusing lens or reflecting lens is used to modify the characteristics of the wave fronts of these waves, thus nearly plane waves are leaving the housing at exit window 17. Emitting surfaces having other shapes might be used, in particular curved emitting surfaces such as those shown in FIGS. 7A to 7C as well as spherical surfaces. To generate waves having nearly plane or divergent characteristics, additional reflecting elements or lenses might be used. The crystals might, alternatively, be stimulated via an electronic control circuit at different times, so that waves having plane or divergent wave characteristics can be formed even without additional reflecting elements or lenses.

Figure 12:
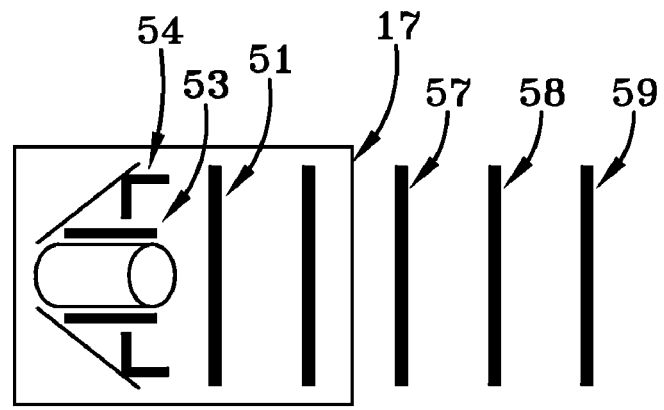
FIG. 12 is a simplified depiction of a pressure pulse/shock wave generator having a cylindrical EMSE system and a triangular shaped reflecting element to generate plane waves. As a result, the pressure pulse/shock waves are leaving the housing via the exit window unfocused having nearly plane wave characteristics.

FIG. 12 is a simplified depiction of the pressure pulse/shock wave generator (shock wave head) comprising a cylindrical electromagnet as a generating element 53 and a first reflector having a triangular shape to generate nearly plane waves 54 and 51. Other shapes of the reflector or additional lenses might be used to generate divergent waves as well.

Figure 13:
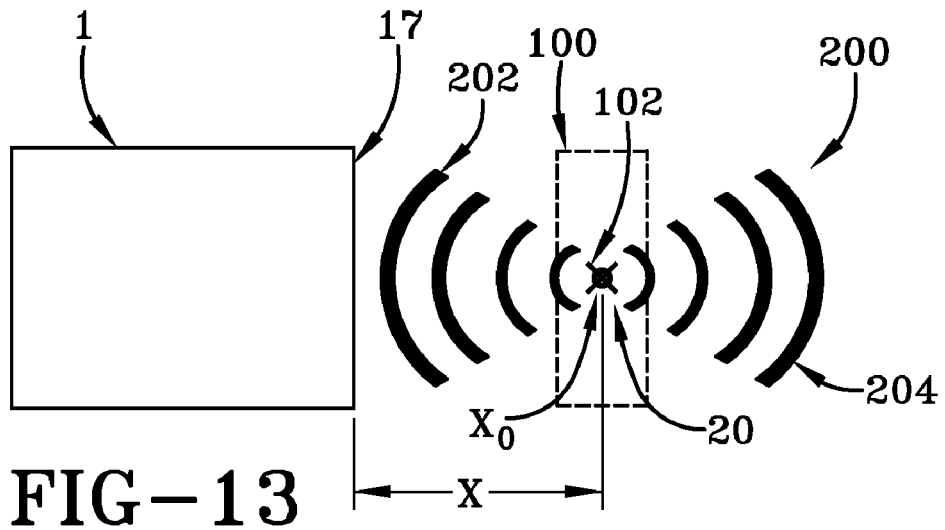
FIG. 13 is a simplified depiction of a pressure pulse/shock wave (PP/SW) generator with focusing wave characteristics shown focused with the focal point or geometrical focal volume being on a substance, the focus being targeted on the location $X_0$.
Figure 14:
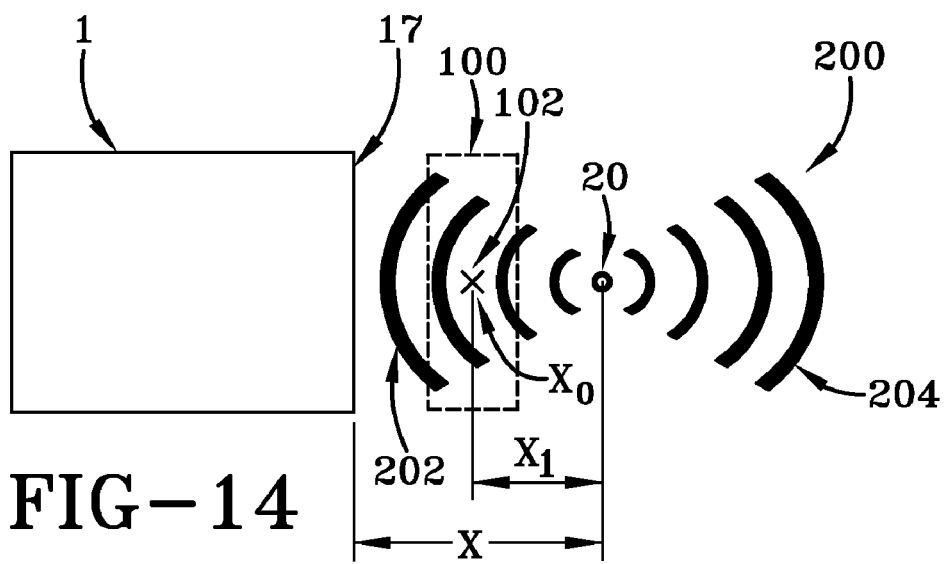
FIG. 14 is a simplified depiction of a pressure pulse/shock wave (PP/SW) generator with the focusing wave characteristics shown wherein the focus is located a distance X, from the location $X_0$ of a substance wherein the converging waves impinge the substance.
Figure 15:
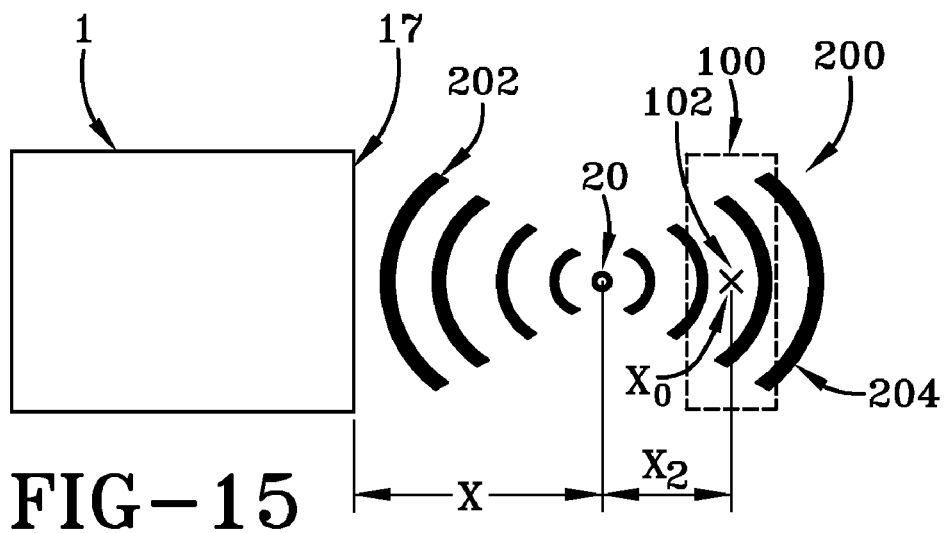
FIG. 15 is a simplified depiction of a pressure pulse/shock wave (PP/SW) generator with focusing wave characteristics shown wherein the focus is located a distance $X_2$ from the mass location $X_0$ wherein the emitted divergent waves impinge the substance.

With reference to FIGS. 13, 14 and 15 a schematic view of a shock wave generator or source 1 is shown emitting a shock wave front 200 from an exit window 17. The shock wave front 200 has converging waves 202 extending to a focal point or focal geometric volume 20 at a location spaced a distance X from the generator or source 1. Thereafter the wave front 200 passes from the focal point or geometric volume 20 in a diverging wave pattern as has been discussed in the various other FIGS. 4-12 generally.

With particular reference to FIG. 13 tissue of a subsurface organ 100 is shown generally centered on the focal point or volume 20 at a location $X_0$ within the tissue of a subsurface organ 100. In this orientation the emitted waves are focused and thus are emitting a high intensity acoustic energy at the location $X_0$. This location $X_0$ can be anywhere within or on the tissue of a subsurface organ. Assuming the tissue of a subsurface organ 100 is a tissue having a mass 102 at location $X_0$ then the focus is located directly on the mass 102. In one method of treating a tumor or any other type mass 102 these focused waves can be directed to destroy or otherwise reduce the mass 102.

With reference to FIG. 14, the substance 100 is shifted a distance X toward the generator or source 1. The tissue of a subsurface organ 100 at location $X_0$ being positioned a distance $X$-$X_1$ from the source 1. This insures the tissue of a subsurface organ 100 is impinged by converging waves 202 but removed from the focal point 20. When the tissue of a subsurface organ 100 is tissue this bombardment of converging waves 202 stimulates the cells activating the desired healing response as previously discussed, this also is one of the preferred methods to treat an inflamed diabetic pancreatic tissue.

With reference to FIG. 15, the tissue of a subsurface organ 100 is shown shifted or located in the diverging wave portion 204 of the wave front 200. As shown $X_0$ is now at a distance $X_2$ from the focal point or geometric volume 20 located at a distance X from the source 1. Accordingly $X_0$ is located a distance $X+X_2$ from the source 1. As in FIG. 10 this region of diverging waves 204 can be used to stimulate the substance 100 which when the substance is a cellular tissue stimulates the cells to produce the desired healing effect or response, this is also one of the preferred methods.

As shown the use of these acoustic wave forms can be used separately or in combination to achieve the desired therapeutic effect.

Furthermore such acoustic wave forms can be used in combination with drugs, chemical treatments, irradiation therapy or even physical therapy and when so combined the stimulated cells will more rapidly assist the body's natural healing response.

The present invention provides an apparatus for an effective treatment of indications, which benefit from low energy pressure pulse/shock waves having nearly plane or even divergent characteristics. For the treatment of those indications, the procedure to locate the area to which the pressure pulses/shock waves are applied often needs to be less accurate than, e.g., when kidney stones are destroyed with focused waves. In fact, sometimes the knowledge of the physique of the subject to be treated is sufficient, so that imaging devices like ultrasound, x-ray or similar, as they are known from devices used in the destruction of kidney stones, may not be required. The area of the focal point/focus volume can be enlarged by reducing the focusing or even by eliminating it all together by using an apparatus according to the present invention which produces waves having wave fronts with nearly plane or divergent characteristics.

With an unfocused wave having nearly plane wave characteristic or even divergent wave characteristics, the energy density of the wave may be or may be adjusted to be so low that side effects including pain are very minor or even do not exist at all.

In certain embodiments, the apparatus of the present invention is able to produce waves having energy density values that are below 0.1 mJ/mm2 or even as low as 0.000 001 mJ/mm2. In a preferred embodiment, those low end values range between 0.1-0.001 mJ/mm2. With these low energy densities, side effects are reduced and the dose application is much more uniform. Additionally, the possibility of harming surface tissue is reduced when using an apparatus of the present invention that generates waves having nearly plane or divergent characteristics and larger transmission areas compared to apparatuses using a focused shock wave source that need to be moved around to cover the affected area. The apparatus of the present invention also may allow the user to make more precise energy density adjustments than an apparatus generating only focused shock waves, which is generally limited in terms of lowering the energy output.

The treatment of the above mentioned diabetic indications are believed to be a first time use of acoustic shock wave therapy. None of the work done to date has treated the above mentioned indications with convergent, divergent, planar or near-planar acoustic shock waves of low energy.

It will be appreciated that the apparatuses and processes of the present invention can have a variety of embodiments, only a few of which are disclosed herein. It will be apparent to the artisan that other embodiments exist and do not depart from the spirit of the invention. Thus, the described embodiments are illustrative and should not be construed as restrictive.

What is claimed is:

1. The method of stimulating a tissue of a subsurface organ comprises the steps of:

treating the tissue of the subsurface organ;

activating an acoustic shock wave generator or source to emit pressure pulses or acoustic shock waves directed toward the tissue of the subsurface organ to impinge the tissue of the subsurface organ with pressure pulses or shock waves having a low energy density in the range of 0.00001 mJ/mm$^2$ to 1.0 mJ/mm$^2$; the pressure pulse being an acoustic pulse which includes several cycles of positive and negative pressure, wherein the pressure pulse has an amplitude of the positive part of such a cycle should be above 0.1 MPa and the time duration of the pressure pulse is from below a microsecond to about a second, rise times of the positive part of the first pressure cycle in the range of nano-seconds (ns) up to some milli-seconds (ms), the acoustic shock waves being very fast pressure pulses having amplitudes above 0.1 MPa and rise times of the amplitude being below 100's of ns, the duration of the shock wave is typically below 1-3 micro-seconds (µs) for the positive part of a cycle and typically above some micro-seconds for the negative part of a cycle;

subjecting the tissue of the subsurface organ to convergent, divergent, planar or near planar acoustic shock waves or pressure pulses in the absence of a focal point impinging the substance stimulating a cellular response in the absence of creating cavitation bubbles evidenced by not experiencing the sensation of cellular hemorrhaging caused by the emitted waves or pulses in the tissue of the subsurface organ wherein the tissue of the subsurface organ is positioned within a path of the emitted shock waves or pressure pulses and away from any localized geometric focal volume or point of the emitted shock waves wherein the emitted shock waves or pressure pulses either have no geometric focal volume or point or have a focal volume or point ahead of the tissue of the subsurface organ or beyond the tissue of the subsurface organ thereby passing the emitted waves through the tissue of the subsurface organ while avoiding having any localized focal point within the tissue of the subsurface organ wherein the emitted pressure pulses or shock waves are convergent, divergent, planar or near planar and the pressure pulse shock wave generator or source is based on electro-hydraulic, electromagnetic, piezoceramic or ballistic wave generation having an energy density value ranging as low as 0.00001 mJ/mm$^2$ to a high end of below 1.0 mJ/mm$^2$.

2. The method of stimulating a tissue of a subsurface organ of claim 1 wherein the emitted shock waves are divergent or near planar.

3. The method of stimulating a tissue of a subsurface organ of claim 1 wherein the emitted shock waves are convergent having a geometric focal volume or point at a distance of at least X from the generator or source, the method further comprising positioning the tissue at a distance less than the distance X from the source.

4. The method of stimulating a tissue of a subsurface organ of claim 1 wherein the tissue is a tissue having cells.

5. The method of stimulating a tissue of a subsurface organ of claim 4 wherein the tissue is an organ of a mammal.

6. The method of stimulating a tissue of a subsurface organ of claim 5 wherein the mammal is a human or an animal exhibiting type 1 or type 2 diabetes condition.

7. The method of stimulating a tissue of a subsurface organ of claim 6 wherein the organ is a pancreas.

8. The method of stimulating a tissue of a subsurface organ of claim 6 wherein the organ is a liver.

9. The method of stimulating a tissue of a subsurface organ of claim 6 wherein the organ is a kidney.

10. The method of stimulating a tissue of a subsurface organ of claim 4 wherein the tissue is a part of the incretin system.

11. The method of stimulating a tissue of a subsurface organ of claim 10 wherein the tissue is a part of the incretin system, including alpha cells, beta cells, neural cells, nerve cells and islets for the production of insulin.

12. The method of stimulating a tissue of a subsurface organ of claim 11 wherein the tissue is a part of the pancreas.

13. The method of stimulating a tissue of a subsurface organ of claim 12 wherein the step of subjecting the tissue to acoustic shock waves creates an analgesic effect on the nerve cells sufficient to deactivate the pancreatic sensory nerves and to thereby stimulate the islets to begin producing insulin normally.

14. The method of stimulating a tissue of a subsurface organ of claim 12 wherein the step of subjecting the tissue to acoustic shock waves reduces the chronic inflammation of islets of the pancreas.

15. The method of stimulating a tissue of a subsurface organ of claim 12 wherein the step of subjecting tissue to acoustic shock waves stimulates the nerve cells of the pancreas to secrete neuropeptides.

16. The method of stimulating a tissue of a subsurface organ of claim 12 wherein the step of subjecting the substance to acoustic shock waves stimulates at least some of said cells within said substance to release or produce one or more of nitric oxygen (NO), vessel endothelial growth factor (VEGF), bone morphogenetic protein (BMP) or other growth factors.

17. The method of stimulating a substance of claim 4 wherein the substance tissue has a pathological condition.

18. The method of stimulating a tissue of a subsurface organ of claim 12 wherein the organ is in a degenerative condition.

19. The method of stimulating a tissue of a subsurface organ of claim 12 further comprises the step of injecting neuropeptide substance P into the pancreas to stimulate the nerve cells and allow islets to produce insulin properly.

20. The method of preventive shock wave therapy comprises the steps of:

identifying a diabetic at risk patient, the patient having an at risk tissue;

treating the at risk tissue;

subjecting the at risk tissue to shock waves to stimulate tissue repair;

activating an acoustic shock wave generator or source to emit pressure pulses or acoustic shock waves directed toward the at risk tissue to impinge the at risk tissue with pressure pulses or shock waves having a low energy density in the range of 0.00001 mJ/mm$^2$ to 1.0 mJ/mm$^2$; the pressure pulse being an acoustic pulse which includes several cycles of positive and negative pressure, wherein the pressure pulse has an amplitude of the positive part of such a cycle should be above 0.1 MPa and the time duration of the pressure pulse is from below a microsecond to about a second, rise times of the positive part of the first pressure cycle in the range of nanoseconds (ns) up to some milli-seconds (ms), the acoustic shock waves being very fast pressure pulses having amplitudes above 0.1 MPa and rise times of the amplitude being below 100's of ns, the duration of the shock wave is typically below 1-3 micro-seconds (µs) for the positive part of a cycle and typically above some micro-seconds for the negative part of a cycle; and subjecting the at risk tissue to convergent, divergent, planar or near planar acoustic shock waves or pressure pulses in the absence of a focal point impinging the at risk tissue stimulating a cellular response in the absence of creating cavitation bubbles evidenced by not experiencing the sensation of cellular hemorrhaging caused by the emitted waves or pulses in the at risk tissue wherein the at risk tissue is positioned within a path of the emitted shock waves or pressure pulses and away from any localized geometric focal volume or point of the emitted shock waves wherein the emitted shock waves or pressure pulses either have no geometric focal volume or point or have a focal volume or point ahead of the at risk tissue or beyond the at risk tissue thereby passing the emitted waves through the at risk tissue while avoiding having any localized focal point within the at risk tissue wherein the emitted pressure pulses or shock waves are convergent, divergent, planar or near planar and the pressure pulse shock wave generator or source is based on electro-hydraulic, electromagnetic, piezoceramic or ballistic wave generation having an energy density value ranging as low as 0.00001 mJ/mm$^2$ to a high end of below 1.0 mJ/mm$^2$.

21. The method of preventive shock wave therapy of claim 20 wherein the step of identifying an at risk patient includes one or more indications of risk based on family history, genetic disposition, physical condition, or blood or tissue analysis.

22. The method of preventive shock wave therapy of claim 20 further comprises the step of testing the at risk tissue to establish measured baseline condition pre shock wave therapy.

23. The method of preventive shock wave therapy of claim 22 further comprises the step of post shockwave therapy testing the treated tissue for comparison to the baseline condition.

* * * * *